US007749261B2

(12) United States Patent
Hansen et al.

(10) Patent No.: US 7,749,261 B2
(45) Date of Patent: Jul. 6, 2010

(54) FORCED AIR WARMING UNIT

(75) Inventors: Gary L. Hansen, Eden Prairie, MN (US); Allen Hamid Ziaimehr, Arden Hills, MN (US); Randall C. Arnold, Minnetonka, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 1026 days.

(21) Appl. No.: 11/363,136

(22) Filed: Feb. 27, 2006

(65) Prior Publication Data
US 2006/0147320 A1 Jul. 6, 2006

Related U.S. Application Data

(63) Continuation of application No. 10/989,135, filed on Nov. 15, 2004, now Pat. No. 7,014,431, which is a continuation of application No. 10/411,431, filed on Apr. 10, 2003, now Pat. No. 6,876,884.

(51) Int. Cl.
*A61F 7/00* (2006.01)
(52) U.S. Cl. .................. 607/107; 607/104; 607/108
(58) Field of Classification Search ............... 607/104, 607/107, 108, 112
See application file for complete search history.

(56) References Cited

U.S. PATENT DOCUMENTS

| 3,724,092 | A | 4/1973 | McCleerey | 34/99 |
| 3,778,851 | A | 12/1973 | Howarth | 5/347 |
| 4,057,861 | A | 11/1977 | Howorth | 5/365 |
| 4,225,775 | A | 9/1980 | Carter | 392/383 |
| 4,321,456 | A | 3/1982 | Ohnmacht et al. | 392/379 |
| 4,701,595 | A | 10/1987 | Okutsu | 392/385 |
| 4,777,802 | A | 10/1988 | Feher | 62/3.3 |

(Continued)

FOREIGN PATENT DOCUMENTS

JP 58142136 8/1983

(Continued)

OTHER PUBLICATIONS

P.O. Fanger, Thermal Comfort: Analysis and Applications in Environmental Engineering, Danish Technical Press, 1970, pp. 5-67.

(Continued)

*Primary Examiner*—Roy D Gibson
(74) *Attorney, Agent, or Firm*—Terrance A. Meador; INCAPLAW (57) ABSTRACT

A forced air warming unit has a casing with inlet and outlet openings. The casing encloses a scroll housing with a curved inside surface in which a blower is disposed. A circuit board in the casing encloses the blower in the scroll housing. At least one opening penetrates the circuit board. A heater plate is disposed between the circuit board and the blower. The blower draws air through the inlet opening, along a first side of the circuit board through the at least one opening into the scroll housing. The blower also forces air along a second side of the circuit board which faces the scroll housing, through air passages in the circuit board, along the first side through the at least one opening, into the scroll housing. The blower accelerates air along the curved inside surface and past the heater plate. Heated, pressurized air exits through the outlet opening.

15 Claims, 9 Drawing Sheets

U.S. PATENT DOCUMENTS

| | | | |
|---|---|---|---|
| 5,243,682 A | 9/1993 | Eberts | 392/370 |
| 5,300,098 A | 4/1994 | Philipot | 607/96 |
| 5,349,161 A | 9/1994 | Bockholt | 219/385 |
| 5,386,644 A | 2/1995 | Lawall et al. | 34/90 |
| 5,620,482 A | 4/1997 | Augustine et al. | 607/107 |
| 5,800,489 A * | 9/1998 | Augustine | 607/107 |
| 5,875,562 A | 3/1999 | Fogarty | 34/97 |
| 6,126,681 A | 10/2000 | Van Duren et al. | 607/96 |
| 6,210,428 B1 | 4/2001 | Augustine et al. | 607/107 |
| 6,230,501 B1 * | 5/2001 | Bailey et al. | 62/51.1 |
| 6,447,538 B1 | 9/2002 | Van Duren et al. | 607/96 |
| 6,524,332 B1 | 2/2003 | Augustine et al. | 607/107 |
| D485,338 S | 1/2004 | Augustine et al. | D22/332 |
| 6,685,731 B2 * | 2/2004 | Kushnir et al. | 607/104 |
| 6,840,955 B2 * | 1/2005 | Ein | 607/108 |
| 6,876,884 B2 | 4/2005 | Hansen et al. | 607/98 |
| 7,089,995 B2 * | 8/2006 | Koscheyev et al. | 165/46 |
| 7,497,870 B2 | 3/2009 | Frey et al. | 607/107 |
| 2002/0144343 A1 * | 10/2002 | Kuiper et al. | 5/81.1 R |
| 2003/0045918 A1 * | 3/2003 | Turner et al. | 607/107 |
| 2004/0153132 A1 | 8/2004 | Cobb et al. | 607/104 |
| 2004/0204748 A1 | 10/2004 | Hansen et al. | 607/104 |
| 2005/0143796 A1 | 6/2005 | Augustine et al. | 607/104 |
| 2006/0212102 A1 | 9/2006 | Frey et al. | 607/104 |
| 2006/0260609 A1 | 11/2006 | Bruening | 128/200.24 |
| 2008/0195184 A1 | 8/2008 | Ziaimehr | 607/104 |

FOREIGN PATENT DOCUMENTS

| | | |
|---|---|---|
| WO | WO 03/086500 A2 | 10/2003 |
| WO | WO 2008/097285 | 8/2008 |

OTHER PUBLICATIONS

C.B. Mahony & J. Odom, Maintaining intraoperative normothermia: A meta-analysis of outcomes with costs. *AANA Journal*. Apr. 1999. v. 67, No. 2:155-164.

Author Unknown, The Climator Range, Howarth Air Engineering Products, Howarth Surgicare Division, date unknown, 6 pages.

Author Unknown, The Howarth Surgicare Microclimator® and Intensive Care Mattress, Howarth Air Conditioning Limited, Surgicare Division, date unknown, 2 pages.

Wedley, Jr., Studies of Temperature Balance After Open-Heart Surgery, Critical Care Medicine, vol. 3, No. 4, Jul.-Aug. 1975, pp. 134-138.

H.E. Howarth, The Howarth Low Air Loss Mattress and Climators, Howarth Surgicare, date unknown, 7 pages.

Request for Reexamination by Patent Owner Pursuant to 37 CFR § 1.510 in U.S. Appl. No. 6,210,428, mailed Feb. 15, 2002.

BPAI Decision on Appeal, Appeal 2008-0589, Reexamination Control No. 90/006,221, Patent 6,210,428, Decided Apr. 28, 2008.

International Preliminary Report on Patentability, PCT/US2007/021551, mailed Aug. 20, 2009.

* cited by examiner

FORCED AIR WARMING UNIT

CROSS REFERENCE TO RELATED APPLICATIONS

This is a continuation of U.S. patent application Ser. No. 10/989,135, filed Nov. 15, 2004, now U.S. Pat. No. 7,014, 431, which is a continuation of U.S. patent application Ser. No. 10/411,431, filed Apr. 10, 2003, now U.S. Pat. No. 6,876, 884, and contains subject matter related to the following applications:

PCT Patent Application Serial No. PCT/US03/11128, published as WO 03/086500 A2, for "PATIENT COMFORT APPARATUS AND SYSTEM", filed Apr. 10, 2003;

U.S. patent application Ser. No. 10/508,319, for "PATENT COMFORT APPARATUS AND SYSTEM", filed Sep. 20, 2004 as the US national phase of PCT/US03/11128; and U.S. Design patent application Ser. No. 29/179,545, filed Apr. 10, 2003, for "FORCED AIR WARMING UNIT", now U.S. Pat. No. D 485,338.

FIELD OF THE INVENTION

The present invention relates generally to thermal comfort. More particularly, the present invention relates to a portable warming apparatus for providing pressurized, thermally conditioned air to a pneumatic, convective device.

BACKGROUND OF THE INVENTION

The human body requires a controlled temperature for normal physiological processes to work properly. Because of this need, the body is endowed with a complex array of systems for regulating thermal homeostasis. The heat of metabolism is substantial and must be exhausted to the surrounding environment to prevent overheating. However if the heat loss is too great, hypothermia may result. For this and other reasons the body is equipped to maintain thermal equilibrium for a broad range of environmental conditions.

Many of the body's mechanisms for achieving thermal equilibrium are automatic (e.g., sweating, shivering, and vasodilatation). These are beyond the conscious control of the individual and usually suffice to keep the core temperature at a constant level. The body also seeks to maintain thermal equilibrium through conscious behavior: altering posture, clothing, or changing indoor temperatures. Thus, the subjective feeling of being hot or cold assists the body in maintaining thermal homeostasis, and these feelings are attuned to the person's surrounding environment.

Normally extreme heat or cold are required to overcome the body's ability to thermoregulate itself. However, certain drugs and anesthetic agents can reduce the body's ability to respond to thermal challenge. This factor makes surgical patients particularly vulnerable to hypothermia, and a variety of devices have been developed to address this situation. For surgical patients, it is important to make up for the loss of automatic thermoregulatory mechanisms. While these patients are anesthetized and unconscious, subjective feelings of discomfort are typically not an issue in their treatment.

However if the patient is conscious, poor thermoregulation can result in acute feelings of discomfort. Even if the patient is clinically normothermic it is still likely that they will experience subjective sensations of "feeling cold". Indeed, this is the primary complaint of many post-surgical patients. Thus, for these patients, preventing or treating hypothermia alone is not sufficient; one must also meet the needs of thermal comfort.

"Thermal comfort" for a person is defined by P. O. Fanger as "that condition of mind which expresses satisfaction with the thermal environment". Fanger, *Thermal Comfort: Analysis and Applications in Environmental Engineering*, Danish Technical Press, Copenhagen, 1970. Now, it is increasingly apparent that making patients thermally comfortable is a desirable clinical objective. Aside from humanitarian concerns, there are many good reasons to provide for the thermal comfort of a patient:

Anxiolysis—the reduction of anxiety has been shown to have beneficial effects in patient outcomes Nursing time—Nurses need not spend their time responding to patients' request for more or different thermal comfort interventions.

Some clinics address their patients' thermal comfort needs by raising the room temperature. This is expensive and unnecessary when patients can control their own microenvironment.

Patient satisfaction is a growing concern among competing hospitals. Lack of thermal comfort is a frequent complaint among patients, and results in poor patient ratings.

Therefore, the provision of means to enable a patient to selectively control the thermal characteristics of his or her own personal microenvironment in a medical setting should produce the following unexpected benefits: 1.) reduced blood pressure and easier IV access; 2.) reduced pain sensation; 3.) normalizing of the patient's perception of time slowing; 4.) reduced anxiety and reduced need for medication. These and other objectives are realized when a patient is maintained in a state of thermal comfort.

DISCUSSION OF THE PRIOR ART

Passive Warming Systems

A variety of means have been used to address the thermal health requirements of patients in a clinical setting. Most commonly used is an insulating layer between the patient and the environment. Added clothing or blankets help the body to retain the heat of metabolism, and may by themselves, be sufficient to achieve thermal comfort. Under an insulating layer, metabolic heating warms a layer of air between the skin and the blanket. The insulating layer, the layer of air between it and a patient, and the patient constitute what may be termed a "microenvironment". Some heat from this microenvironment is lost to the insulating layer; and some of this heat, in turn, is lost to surrounding room air. The important effect is that the air pocket under the insulating layer reaches an equilibrium temperature somewhat warmer than the room air. The problem with any form of insulating covering is that it makes access to the patient more difficult for the physician.

Sometimes blankets are pre-warmed. Rarely are they made warmer than the skin surface itself, so there is little if any transfer from the blanket to the body. Rather, pre-warming prevents the initial transfer of heat from the skin to the cool blanket. Given enough time, even a warmed blanket will come to thermal equilibrium with both the body and the surrounding room air. This cool-down takes time, and the final result will be the same as with a non-warmed blanket. This time is usually quite short (3-5 minutes), which requires frequent attention of the nursing staff.

It is possible to increase the insulating value of the blanket, reduce its thermal mass, or both. However, all means for doing so must rely on the body's own internal heat to warm the microenvironment.

Active Warming Systems

There are devices that augment metabolic heating in the task of keeping the microenvironment near the skin warm. If the air in the microenvironment is warmer than the skin surface, some heat will enter the body. But even if the microenvironment is cooler than the skin, it can assist in preventing further heat loss. Such devices maintain a microenvironment that is warmer than is possible with passive systems.

One family of devices relies on heat conduction, where a heated region contacts the skin surface. Examples include electrical resistance heaters (e.g., heating pads), heated waterbeds or blankets, and other mechanisms that try to infuse heat directly through the skin. While conduction is very efficient means to transfer heat, it is difficult to design a device that uniformly covers large areas of the body. Uneven distribution of heat, if large enough, can result in thermal discomfort. Further, if such devices are applied directly to the skin of a patient, the combination of pressure and heat can result in burn injury.

A second family of devices relies on heated air convection. Here, warm air is circulated through the air pocket, warming the skin surface and also the insulating blanket. There may still be convective and conductive heat loss from the system, but the additional heat reduces or eliminates the need for the body to maintain the warmth of its microenvironment. Examples of this device include the Bair Hugger® family of products available from Arizant Healthcare Inc., the assignee of this patent application.

Patient-Controlled Medical Systems

The temperature requirements for thermal comfort are highly variable. They depend on the environment, and also on the personal and subjective factors. As a result, people usually desire to have direct control over their own thermal environment. Thus thermostats allow the room temperature to be set to a (single) individual's preference. Even the common electric blanket frequently has multiple adjustments: one for each user. The prior art contains many such references.

In the medical area, there are some temperature-control devices with individual settings, but the decision to establish and change those settings is typically in the hands of the clinician, not the patient. Also, the heat output of such devices may be high enough so that it would be unsafe to leave the temperature setting to an untrained person. Also, temperature settings on current devices are often coarse, not providing sufficient sensitivity for individual preference.

Nonetheless, experience in non-thermal devices (e.g., patient controlled pain management devices) shows that patients benefit strongly from having comfort-based decisions within their own control.

BRIEF SUMMARY OF THE INVENTION

The invention itself consists of a forced air warming unit to be used with a heat applicator including a pneumatic convective device and a hose that connects the forced air warming unit with the device.

The forced air warming unit may be provided with a manually-operated remote control for use by a patient. The forced air warming unit pressurizes and heats air and is adapted to provide pressurized, heated air to an air hose for delivery there through to a pneumatic convective device. The forced air warming unit also includes electronic components that regulate the temperature and pressure of air output of the device and ensure that the temperature never reaches unsafe levels.

The manually-operated remote control includes means for the patient to make fine adjustments to the unit's output temperature, and also to turn the device on or off.

BRIEF DESCRIPTION OF THE DRAWINGS

A more complete understanding of the present invention may be derived by referring to the detailed description and claims when considered in conjunction with the following Figures, wherein like reference numbers refer to similar elements throughout the Figures.

DETAILED DESCRIPTION OF A PREFERRED EMBODIMENT

The invention concerns a forced air warming unit and more particularly, one with a manually-operated remote control available for use by a person in controlling thermal conditions of his or her own personal microenvironment to achieve and maintain a personalized state of thermal comfort in a clinical setting.

Figure 1:
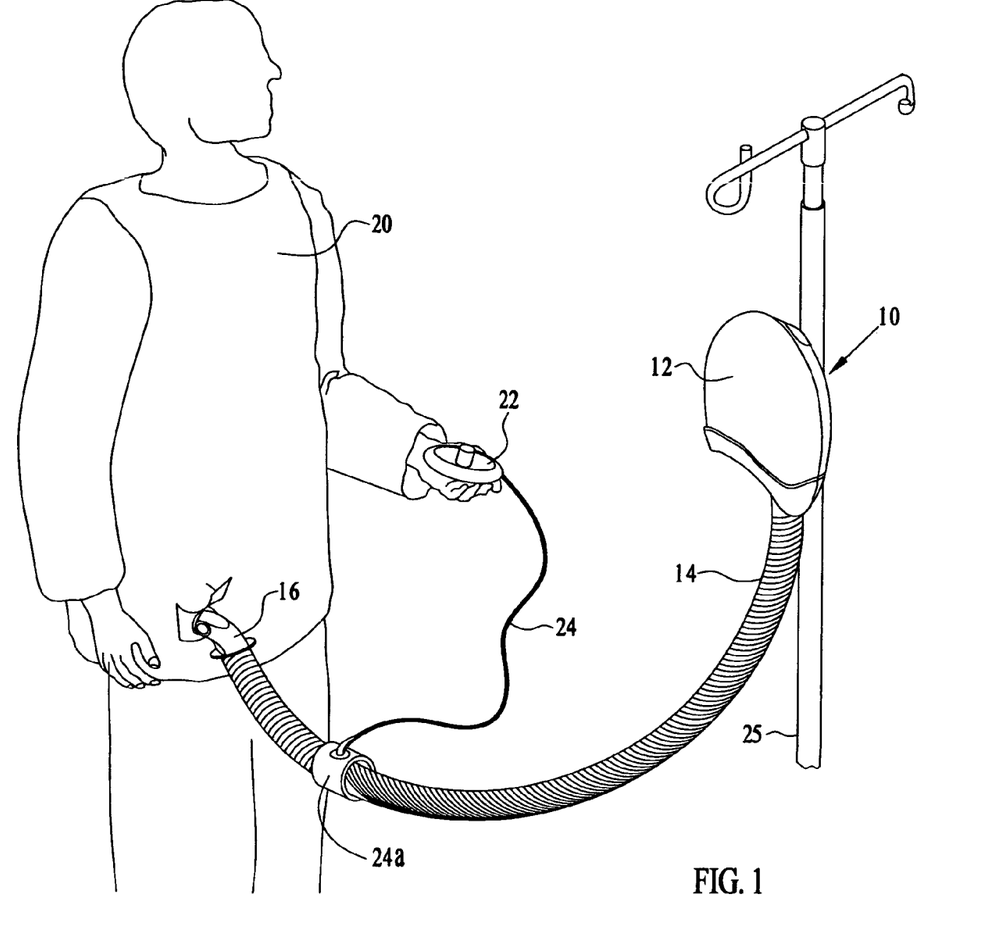
FIG. 1 is shows the forced air warming unit in use in a clinical setting.

FIG. 1 illustrates the invention deployed for use in a clinical setting. In this regard, the invention extends to a forced air warming unit 10 for pressurizing and heating air in a casing 12. One end of an air hose 14 is connected to the casing 12, and the other end of the air hose is connected by a connector 16 to a pneumatic, convective device (not shown) which is disposed within a clinical garment 20 worn by a person in a clinical setting. In operation, the forced air warming unit 10 produces a stream of pressurized, heated air which exits the casing 12 into the one end of the air hose 14. The stream of pressurized, heated air is conducted by the air hose 14 to the pneumatic, convective device. The pneumatic, convective device receives the stream of pressurized, heated air, distributes the pressurized air within a pneumatic structure, and emits the air through one or more surfaces for convective transfer of heat between the thermally conditioned air and the body of the person wearing the clinical garment 20. The forced air warming unit 10 may have provisions for mounting on an IV pole 25.

Although the forced air warming unit is intended for use with an air hose and a pneumatic convective device, neither of these elements is necessary to the building and operation of this invention. Examples of pneumatic convective devices with which the invention may be used are found in the above-referenced patent application entitled "PATIENT COMFORT APPARATUS AND SYSTEM", both of which are incorporated herein by this reference.

A manually-operated remote control 22 is connected by signal cable 24 to control circuitry (not shown) disposed within the casing 12. The remote control 22 enables the person wearing the clinical garment 20 to control the thermal state of the stream of air produced by the forced air warming unit 10 and thereby to control the temperature of the his or her microenvironment.

Figure 2:
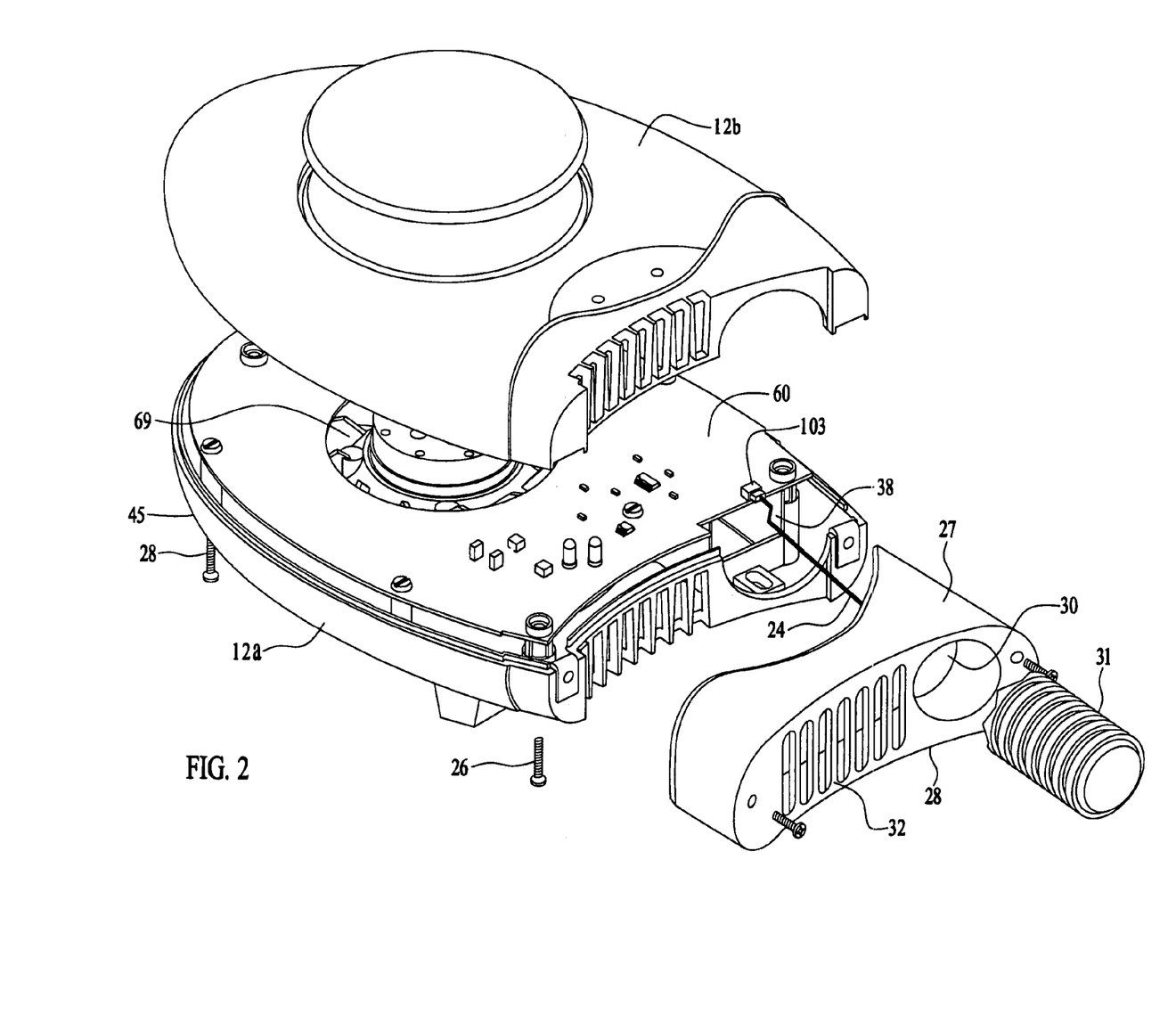
FIGS. 2 and 3 show perspective exploded views of the forced air warming unit.
Figure 3:
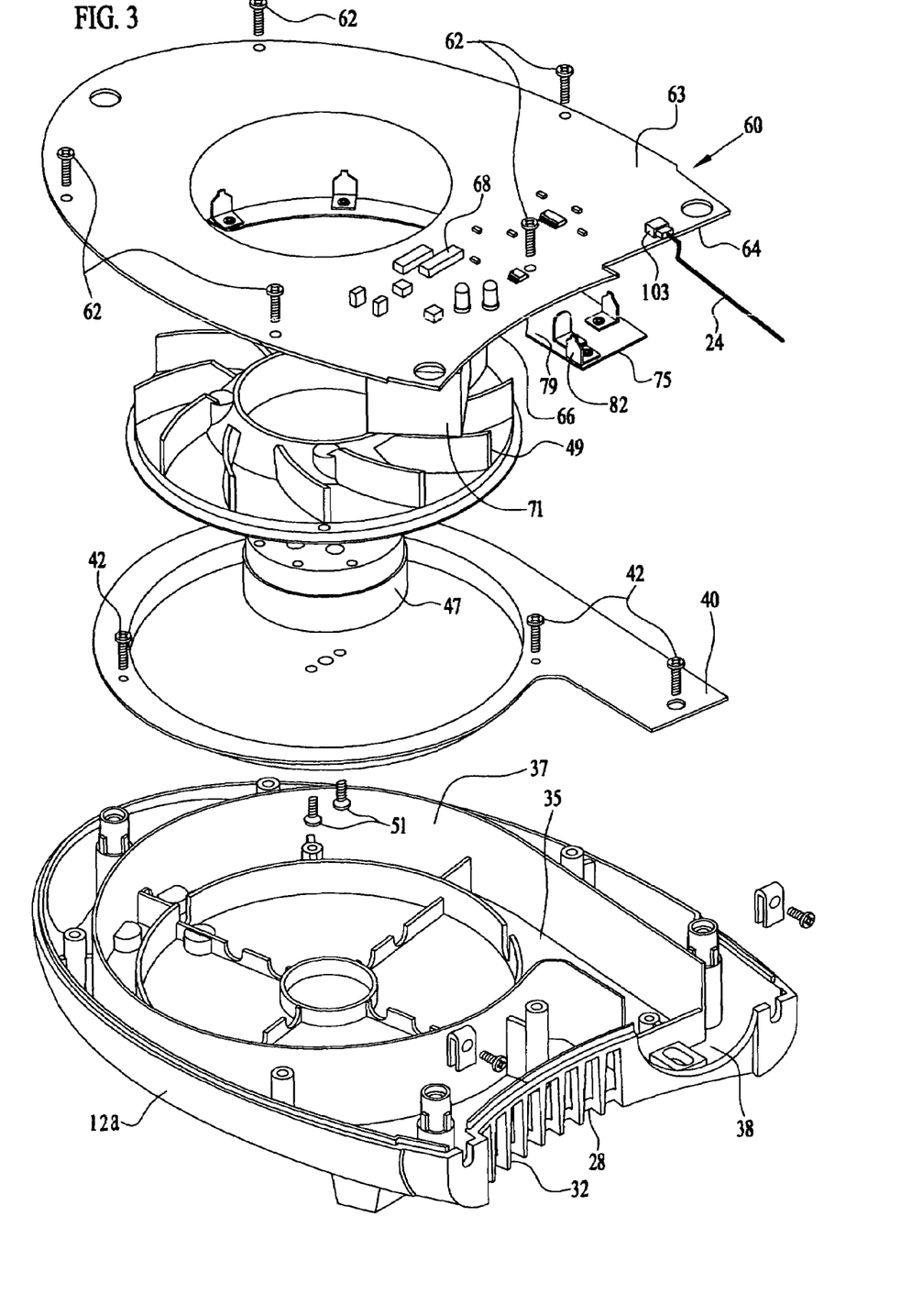

FIGS. 2 and 3 are perspective exploded views showing the arrangement of elements of the forced air warming unit 10. The unit 10 includes a casing 12 having first and second halves 12a and 12b that are joined by threaded screws 26. A shaped end piece 27 defines an edge 28 of the casing 12. The edge 28 has an outlet opening 30 to which an adapter 31 is fitted for receiving and retaining the end 31 of an air hose. The edge 28 has a grated intake opening 32.

A scroll housing 35 with a curved inside surface 37 is fixed by threaded screws (not shown) in the casing half 12a. The scroll housing has an air diffusing outlet 38 positioned near the outlet opening. The casing halves, the end piece, and the scroll housing may all be molded plastic pieces.

A motor mounting plate 40 is fixed by threaded screws 42 to the casing half 12a. The motor mounting plate may be milled or stamped from a thin metal sheet. A radial blower unit 45 includes a motor 47 to which is mounted an impeller 49. We have, for example, used the motor from the Series RER 125 AC radial blower available from EBM Industries, Inc., Farmington, Conn. The radial blower unit 45 is fixed by threaded screws 51 to the motor mounting plate 40, and is positioned generally centrally in the scroll housing 35.

Figure 4:
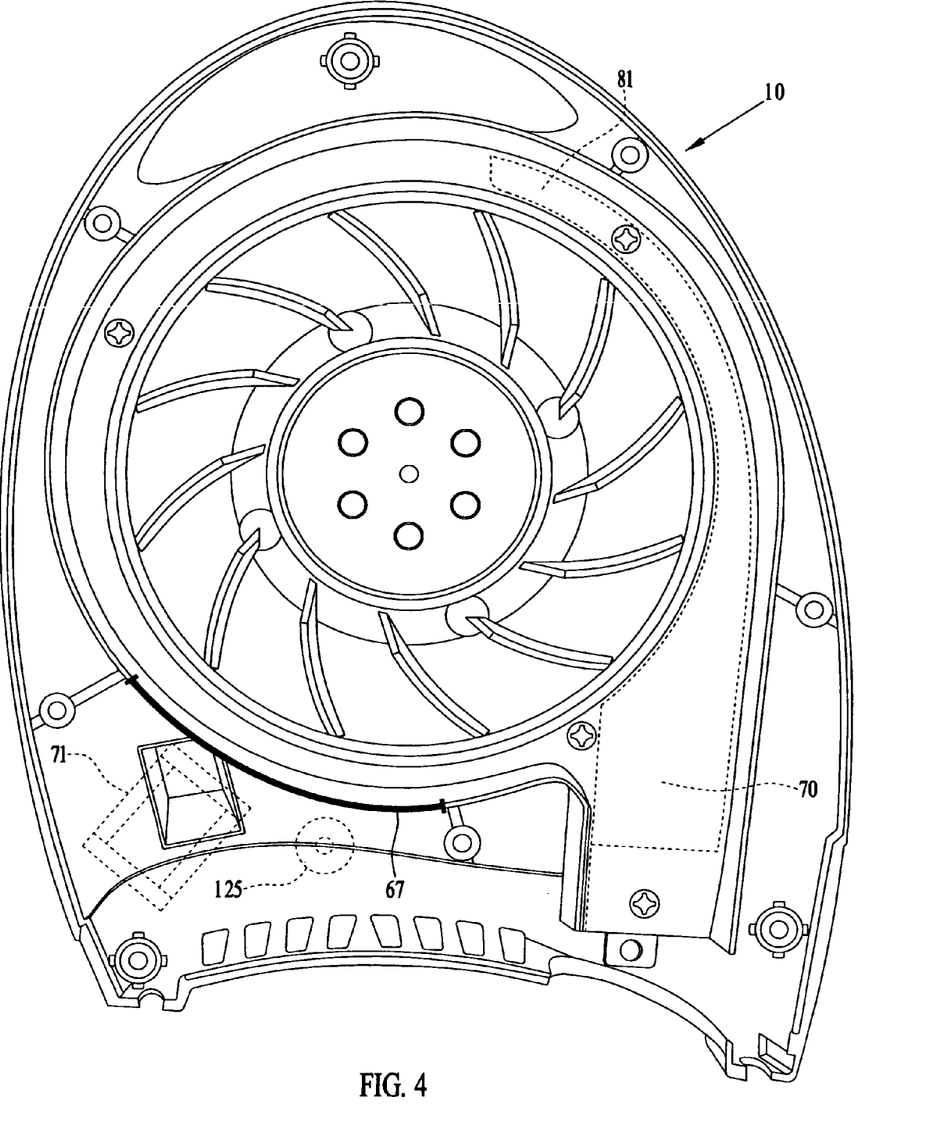
FIG. 4 is a plan view of the forced air warming unit with a portion of the casing removed.

A circuit board 60 is supported by the scroll housing 35 and fixed to the casing half 12a by threaded screws 62. The circuit board has a conventional multilayer construction with a first side 63 which faces the casing half 12b, a second side 64 facing and supported on the scroll housing 35, and a forward edge 66 disposed near or adjacent the intake opening 32. As best seen in FIG. 4 there is a series of passages, cuts or holes 67 through the circuit board near the forward edge 66 that form airflow passages from circuit board side 64 to 63. There is also an opening 69 in the circuit board that is centered on the motor 47. Control circuitry 68 is mounted by conventional solder technology on the first side 63, and power conversion apparatus, including a transformer 71, is mounted on the second side 64, near the intake opening 32, just forward of the passages 67.

Figure 5:
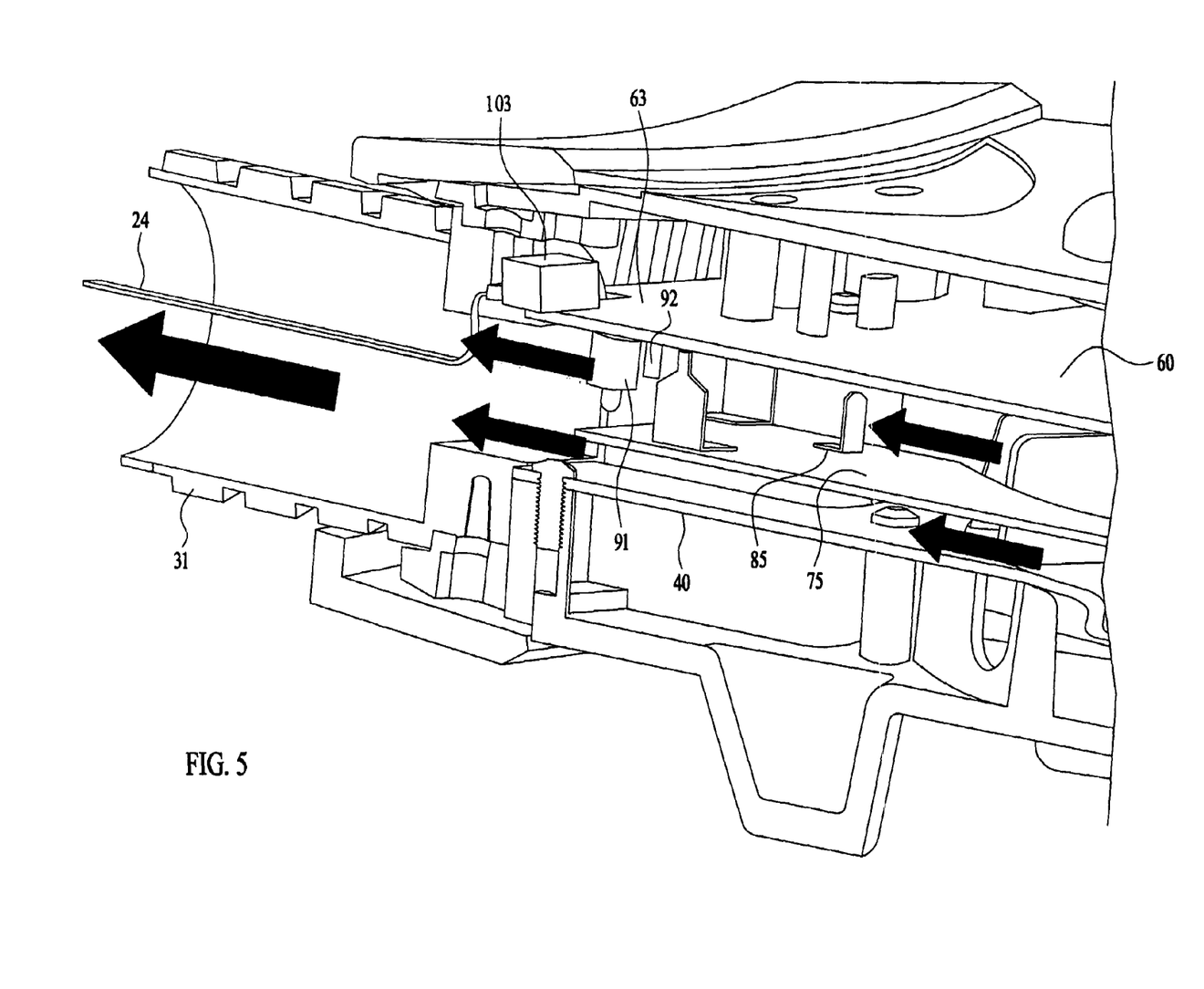
FIG. 5 is a sectional view showing details of the forced air warming unit; details of the forced air warming unit.

Referring to FIGS. 2-5, a heater plate 75 is supported in the scroll housing 35, near the diffusing outlet 38. In the preferred embodiment, the heater plate 75 is an elongate, tapered, curved metal piece having a relatively wider first end 79 positioned near the diffusing outlet 38 and a relatively narrower second end 81 positioned in the scroll housing 35 between the impeller 49 of the radial blower unit and the curved inside surface 37 of the scroll housing. The heater plate 75 has standoffs 82 by which it is soldered to the second side 64 of the circuit board 60. As best seen in FIG. 5, the heater plate 75 is positioned between the circuit board 60 and the motor mounting plate 40. The heater plate 75 is wound with a thin metallic electrical conductor (not shown) which itself is connected to the control circuitry 68. In FIG. 5 one may see a turbulator 85 mounted on the side of the heater plate 75 facing the circuit board 60. One or more such devices may be similarly disposed in the air diffusing outlet 38 of the scroll housing; it is not necessary to the invention that they be mounted on the heater plate.

Figure 6:
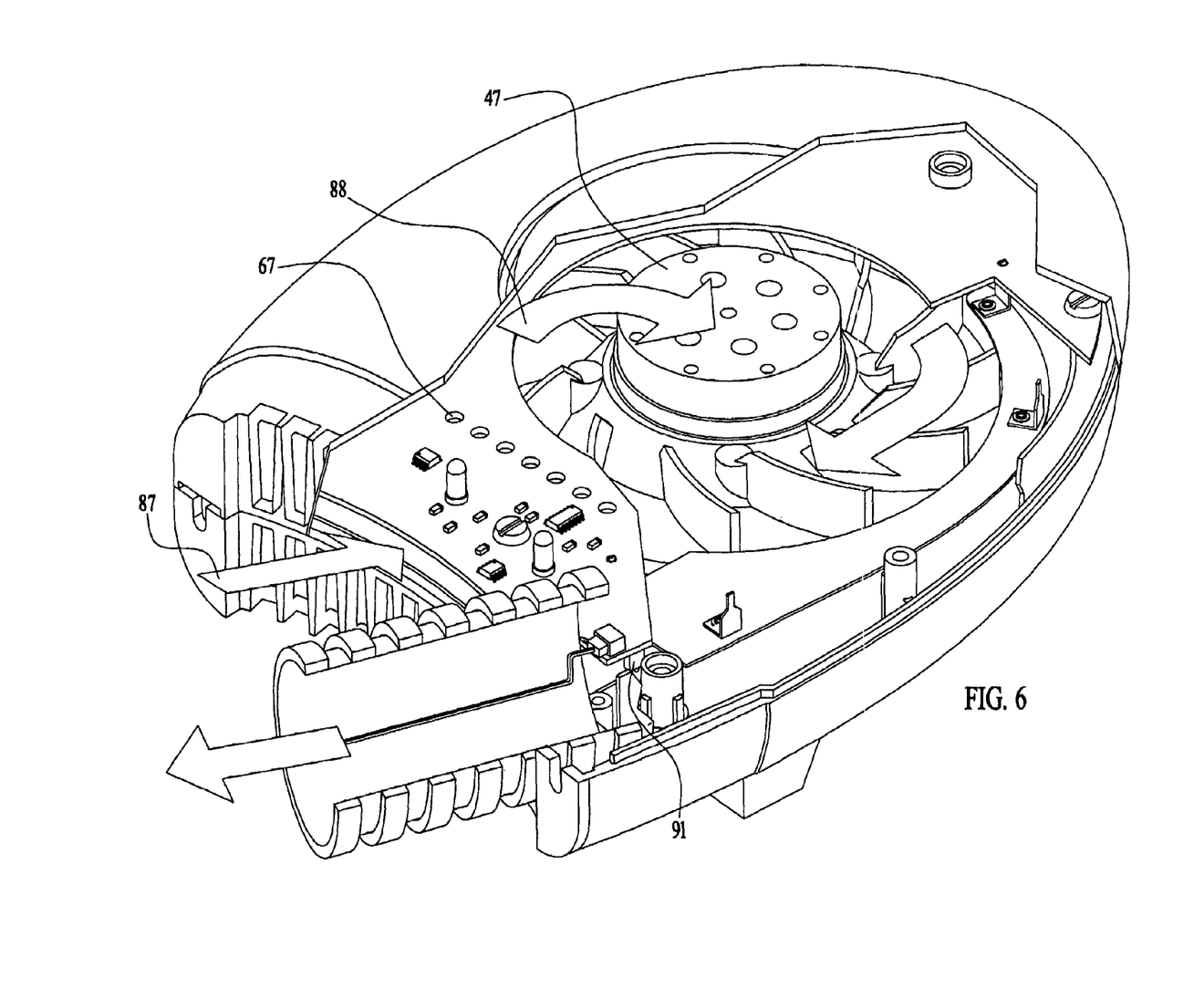
FIG. 6 is a perspective view with portions of the casing removed showing details of the forced air warming unit.

With reference to FIGS. 4-6, in the operation of the forced air warming unit 10, the motor 47 is energized by provision of drive power from the power conversion apparatus, causing the impeller 49 to rotate in a clockwise direction (in the views presented in FIGS. 4 and 6), which pressurizes and forces air in the scroll housing 35 to move against the curved inside surface 37 toward and through the air diffusing outlet 38 for provision to adapter and, from there, to the end of the air hose 31. In response, air is drawn into the unit 10 through the intake opening 32. Once through the intake opening 32, the air is drawn into the scroll housing 35, principally along two air intake flow paths. The first air intake flow path, represented by the arrows 87 and 88 in FIG. 6, is through the intake opening 32, past the forward edge 66 and along the first side 63 of the circuit board, through the opening 69, and into the scroll housing 35. Air flow along this path cools the control circuitry 68, the first side 63 of the circuit board, and the motor 47. The second air intake path is through the intake opening 32, past the forward edge 66 and along the second side 64 of the circuit board, through the passages 67, along the first side 63 of the circuit board, through the opening 69, and into the scroll housing 35. Air flow along this path cools the power conversion apparatus, including the transformer 71, the second side 64 of the circuit board, and the motor 47.

As air is pressurized by and flows through the scroll housing 35, current is provided to the windings on the heater plate 75, raising the temperature of the heater plate 75 and thereby the temperature of pressurized air as it is forced through the scroll housing 35 to the diffusing outlet 38. In the diffusing outlet, the pressurized, heated air flows past the one or more turbulators 85.

Design constraints, which included a desired small size of the forced air warming unit 10 and limitation of cost, dictate a unit 10 with a minimal number of electrical and mechanical components. One result is that the same electrical circuit activates the blower unit and heater plate windings. Another result is the choice of a blower unit that comes up to speed slowly. As best seen in FIG. 5, the small size of the unit 10 forces control and temperature sensors 91 and 92 that provide sensor outputs to the control circuitry 68 to be located on the second side 64 of the circuit board in close proximity to the first end 79 of the heater plate 75, in the air diffusing outlet 38. Due to uneven distribution of obstacles and forces within the scroll housing 35, flow at that location was found to be extremely non-linear, characterized by a large temperature range of about 35° to 90° C., and with a flow range of about 5 to 15 CFM (cubic feet per minute). The one or more turbulators 85 help even out the temperature profile around the sensors.

Figure 7:
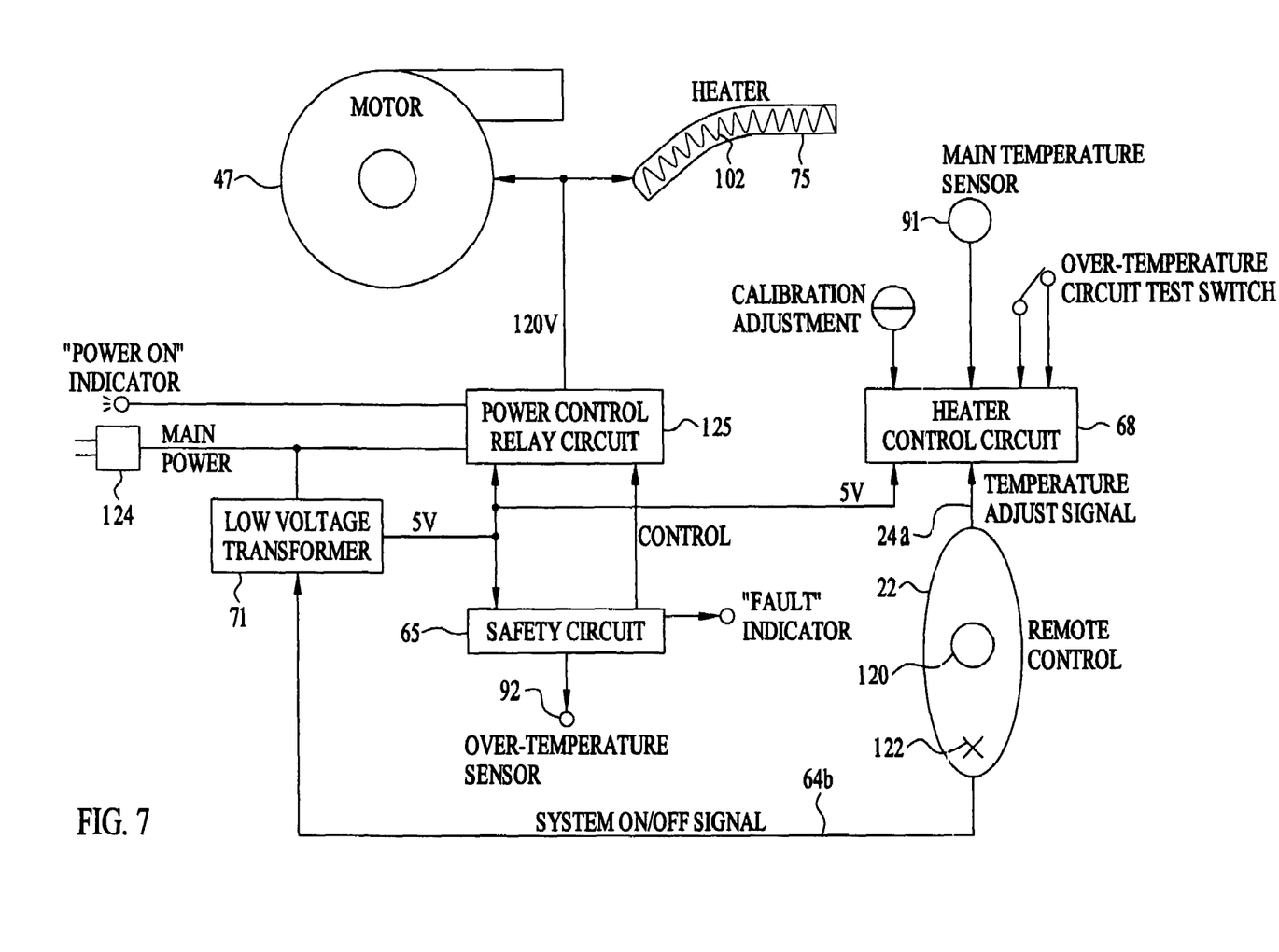
FIG. 7 is a schematic diagram of the forced air warming unit.

FIGS. 1, 3, and 5 illustrate a preferred way of coupling the manually-operated remote control 22 to the control circuitry 68. The remote control 22 has a signal cable 24 that penetrates into the interior of the air hose 14 through the coupling 24a. The cable 24 itself may have the capacity to transfer more than one control signal, and indeed may have more than one signal path. Inside the air hose, the signal cable extends to and through the adapter 31, connecting to the control circuitry 68 through a plug 103 mounted on the first side 63 of the circuit board, near the forward edge 66. Refer now to FIG. 7 for an understanding of the functional architecture by which the operations of the forced air warming unit 10 are controlled. The remote control 22 includes two controls, one (temperature control) for control of the thermal condition of pressurized, heated air produced by the unit, the other for regulating high voltage functions of the unit. The temperature control preferably includes a hand-operated potentiometer 120 affording a continuously-variable control signal which is provided to the control circuitry 68 through the signal cable 24. The magnitude of the control signal causes the control circuitry 68 to set the current through the windings of the heater plate 75. This permits user control and variation of the thermal state of the pressurized air that enters the user's microenvironment. The second control includes an on-off switch 122.

In other embodiments, the patient might be given the control of air pressure and air speed as well. The remote control may communicate with the control circuitry by means of a wire tether, IR signals, radio signals, or other means. A further embodiment may combine the remote control and the control circuitry into a base station comprising one small unit that resides near the patient.

Thermal Comfort: Experimental Considerations
Performance Requirements of the Invention As described above, there are many possible ways to warm a patient in a clinical setting. If the intent is to treat or prevent hypothermia, little attention needs to be paid to subjective feeling of the patient—the problem is merely an exercise in heat transfer theory. However, if the needs of thermal comfort are considered, as is the case with our invention, the problem becomes much more stringent. In this case, the target temperature range of the microenvironment is then critical. Also, the heating mechanism must be reasonably uniform over the body. Any large temperature variations are likely to result in discomfort. (ASHRAE Handbook, "Physiological Principles of Thermal Comfort", chapter 8.)

Our conclusion is that control of the microenvironment must be given to the patient, for only the patient knows the specific point at which thermal comfort is provided.

Forced-Air Warming in a Clinical Environment
Arguments for Individual Control of Temperature The exact requirements for thermal comfort have been the object of study for many years. Fanger has studied these requirements in depth and lists six factors that that are necessary and sufficient to predict thermal comfort. (See, Fanger "Assessment of Man's Thermal Comfort in Practice", *British Journal of Industrial Medicine,* 1973, 30, p. 313.)

Air temperature
Radiant temperature
Air velocity
Humidity
Activity level
Clothing It is notable that none of these factors is under the control of a patient who is confined to a bed in a hospital setting. Even without the effects of anesthesia considered, it is not surprising that patients are frequently uncomfortable while undergoing medical treatment.

In this invention, we chose to adjust the variable of air temperature to address the problem of thermal discomfort. We therefore had to consider the range of temperatures necessary to cover the majority of individuals and the degree of sensitivity afforded by adjustment.

Fanger teaches that for normal conditions, and all of other factors well controlled, the vast majority of people seek to have their skin temperature at about 35° C. This, he holds, is independent of age, sex, or ethnicity. Based on large worldwide population studies, he found that it is possible to determine a single optimal combination of the above factors that optimize thermal comfort for about 95% of all people.

Fanger's results appear counterintuitive given common sense observations that some people seem more vulnerable to cold than others, and that it is difficult to get any group of people to agree on a comfortable setting for their home of office thermostat. We conclude that Fanger's requirements for thermal comfort are not consistently applicable in real-world applications. This is not because Fanger is wrong, but because actual conditions are rarely as well controlled as those found in medical research. Our invention is designed to address the needs of this real-world condition.

In developing this invention, we performed our own human tests, under conditions that mimic those found in a clinic or hospital. While Fanger specifically sought controlled steady-state conditions, we were more interested in how an individual responds to thermal challenge. In our tests, subjects were subjected to a moderately cool environment for a period of time ("cold soak"), followed by a warm-up session with the forced air warming unit. Patients were given control of the temperature and asked to seek the setting that provides maximum thermal comfort.

Figure 8:
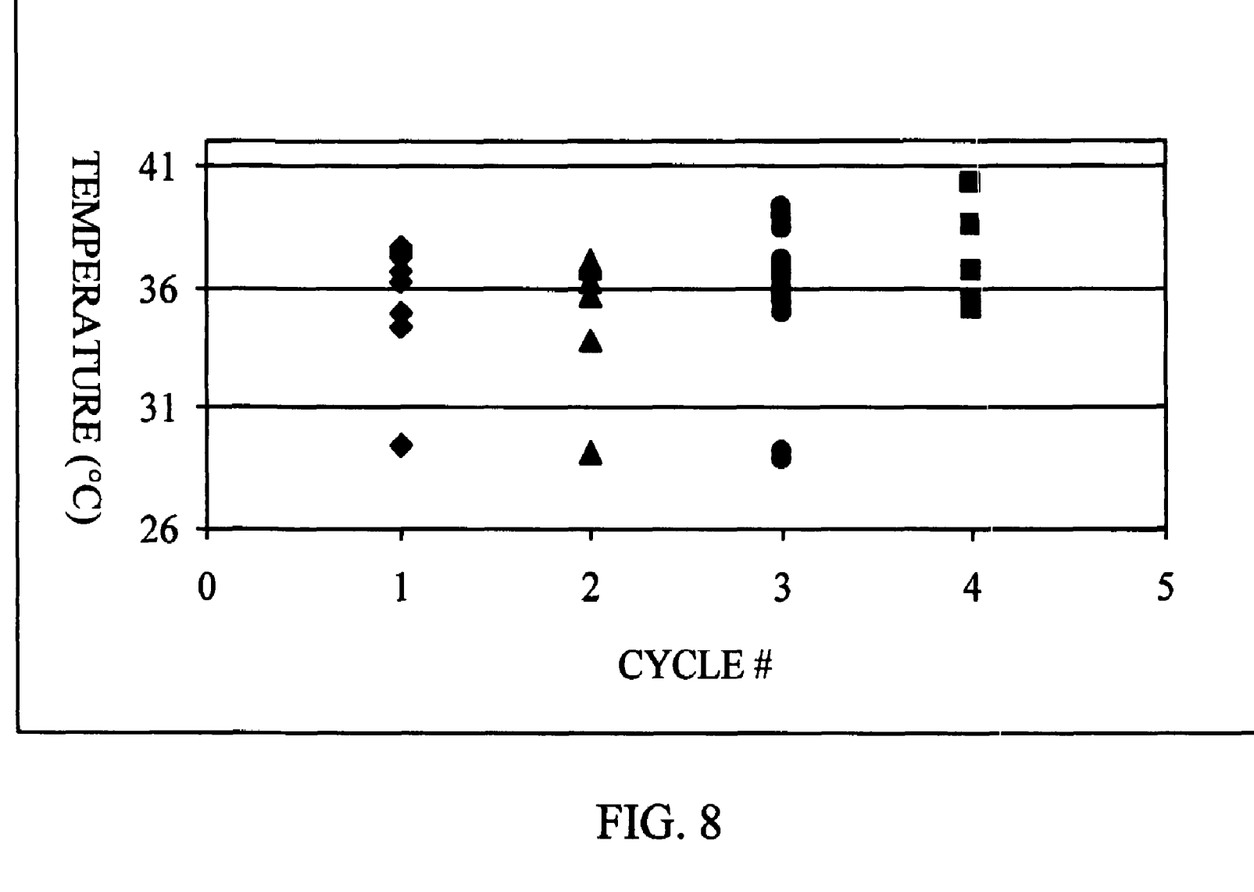
FIG. 8 is a chart showing the variation among optimal comfort settings for various test subjects.

We found that there was substantial variation in person-to-person preferences after the cold soak. Some subjects turned the heat up to maximum, left it there, and still complained that it was not sufficient. Others preferred modest levels of heat and had little trouble achieving thermal comfort. FIG. 8 shows the variation among optimal comfort settings for various people. Although the average was about 36° C., a few people preferred settings as high as 41° C. and as low as 30° C.

We speculate that there are other factors, beyond Fanger's canonical six, that affect thermal comfort in a non-steady-state condition. These factors alter the ability of the subject to respond to a thermal challenge.

Previous environment—coming from a cold/warm room
Previous physical activity
Metabolism differences
Difference peripheral blood circulation
Drugs—(principally caffeine and nicotine)
All of these factors support the argument that patient control is important in non-steady-state conditions, and that no single temperature setting will satisfy most people.

Our tests also showed that for a single individual, the preferred temperature setting changed with time. It was typical (but not universal) pattern to begin with a warmer setting and then turn down the device with time. (See FIG. 9)

Figure 9:
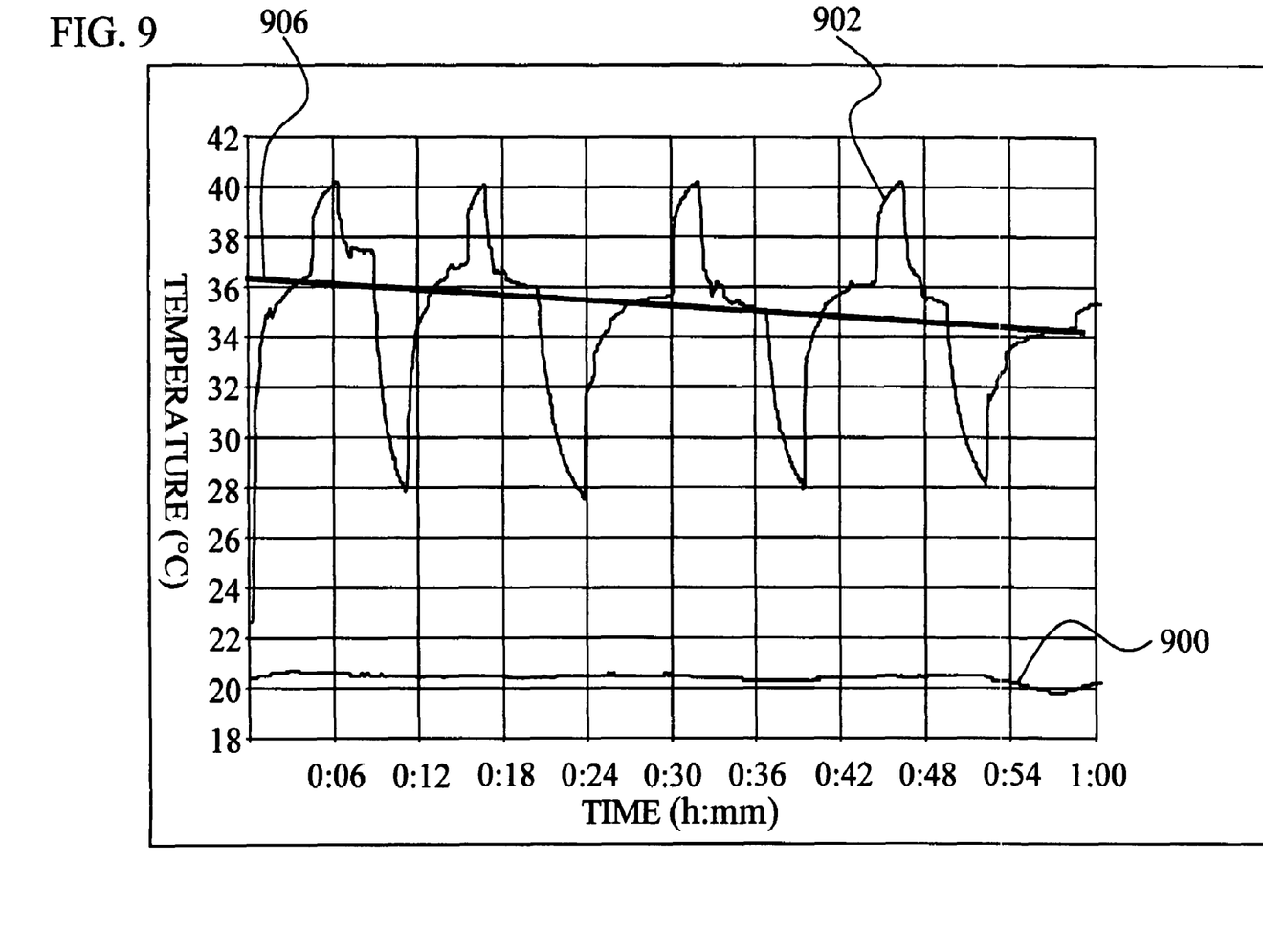
FIG. 9 is a chart showing a test subjects preferred temperature settings change with time.

The tests illustrated in FIG. 9 utilized the combination of elements shown in FIG. 1, with a remotely-controlled forced air warming unit according to this invention connected to a pneumatic convective device mounted to a clinical garment worn by the test subjects. In these tests, in an environment with an ambient temperature indicated by the plot 900, the temperature setting on the remote control was periodically disturbed upward or downward by the researcher. The effect was measured in the nozzle temperature of warmed, pressurized air exiting the air hose into the pneumatic convective device, with the researcher's disturbance shown in steeply rising and falling sections of the curve 902. The subject was then asked to use the remote control unit reset the temperature for the subject's maximum level of comfort. Subject control of the temperature is shown in the relatively slowly changing sections of the curve 902. The results told us two things. First, people's chosen comfort settings definitely changed with time, with a characteristic downward trend 906 over a period of 20-30 minutes.

We believe that the causes of this phenomenon is the time it takes to warm up the micro-environment, equipment, and the person's own periphery (i.e., arms and legs). Assuming that these things are still cool from the cold soak, it takes time to bring them up to approximately body temperature. Additionally, the efficiency of the person's metabolism will also affect the changing heat balance of the system. Also, there is probably a psychological impetus to obtaining as much heat as possible when one is cold.

Second, on a much smaller time scale (3-5 minutes) there was a "threshold of perception" for comfort settings. It is known that people cannot distinguish temperature difference if they are small enough. This will vary from person to person, and also differ on the part of the body exposed to the heat. For this system, under actual conditions of use, we found the threshold to be about 1° C.

The only other consideration in selecting the temperature for a pneumatic, convective warming device is safety. If too much heat is delivered to the patient in too short a time, thermal injuries could result. This upper temperature threshold is provided by Stoll and Greene (Stoll A M, Greene LC. Relationship Bewteen Pain and Tissue Damage Due to Thermal Radiation. J Appl Physiol 1959; 14(3):373-382.) who disclose that temperatures less than 43° C. pose little risk of burning patients, even when prolonged for an extended period of time.

Thus we conclude:
A comfort warming device for clinics and hospitals should be patient controlled
The temperature range may go as low as ambient, but must not exceed 43° C.
Because the threshold of perception is so small, temperature control should be sensitive enough to allow fine adjustments of less than 1° C. For convenience, we selected an analog control, but other control methods allowing fine adjustment are also possible.
Operating Ranges Design of a forced air warming system must consider three main variables. The first, air temperature, has been treated at great length above. The two remaining variables are airflow and air pressure. Both of these factors are critical to the function of the device because they have a direct influence on the amount of heat delivered to the microenvironment.

The upper and lower limits of these variables will depend on the device, but a few general principles apply.

If airflow through a pneumatic convective device is too low, temperature nonuniformity will result across the device. This creates uncomfortable "hot spots". Also, low flow causes more heat to be lost from the air as it moves through the hose connecting the forced air warming unit to the blanket. To compensate, the unit must generate a higher temperature in the warming unit.

If airflow is too high, the sensation of jetting from the device may irritate the subject.

If pressure is too low the device becomes flaccid and is easily obstructed.

If pressure is too high, the device becomes rigid and uncomfortable for the subject. Pressures higher than this may exceed the strength of the material of which the device is made.

For our preferred embodiment, optimal airflow is found between 6 and 15 CFM. Optimal pressure is found between 0.3 inches $H_2O$ and 1.0 inches $H_2O$. These values will of course vary depending on the specific design and materials used for the hose and clinical garment. Subsequent testing of devices within this range has shown these assumptions to be valid. Pressure and temperature may be measured at any point in the system. For example, the hose end could be used or a small canulae may be inserted into the inflated portion of the gown in close proximity to the hose connection. The pressure measuring device may be an analog or digital manometer. The temperature measuring device may be a digital thermocouple. Flow is measured at any convenient point along the hose by means of a vane anemometer.

What is claimed is:

1. A system to provide pressurized, thermally-treated air to a convective warming device by way of an air hose, comprising:
    a forced air warming unit for providing a stream of pressurized, warmed air to an air hose;
    a heater in the forced air warming unit;
    a control circuit in the forced air warming unit, the control circuit connected to the heater; and
    a manually-operated remote control unit external to the forced air warming unit, the remote control unit coupled to the control circuit for causing the forced air warming unit to provide pressurized air in a temperature range of about 27° C. to about 41° C.; and
    further including: a clinical garment with a convective warming device mounted therein; and an air hose connecting the warming device with the forced air warming unit.

2. The system of claim 1, wherein the remote control unit includes a first control for controlling the temperature of the pressurized air, further including a signal cable mounted to the air hose and connecting the first control to the control circuit.

3. The system of claim 2, wherein the remote control unit includes a second control and the signal cable also connects the second control to the control unit for regulating high voltage functions of the forced air warming unit.

4. The system of claim 3, wherein the first control includes a hand-operated potentiometer.

5. A method for warming a person using a forced air warming unit, comprising:
    clothing the person in a clinical garment with a convective warming device mounted therein;
    connecting an air hose between the convective device and the forced air warming unit; and
    controlling the forced air warming unit with a manually-operated remote control unit to provide pressurized air to the convective warming device in a temperature range of about 27° C. to about 41° C.

6. The method of claim 5, further including providing the warmed pressurized air to the convective warming device at a pressure in the range of between 0.3 inches $H_2O$ and 1.0 inches $H_2O$.

7. The method of claim 5, further including providing warmed pressurized air to the convective warming device at a flow rate of between 6 cubic feet per minute and 15 cubic feet per minute.

8. A method for warming a person using a forced air warming unit, comprising:
    clothing the person in a clinical garment with a convective warming device mounted therein;
    connecting an air hose between the convective device and the forced air warming unit;
    controlling the temperature of pressurized air produced by the forced air warming unit with a manually-operated remote control unit; and
    providing warmed pressurized air to the convective warming device at a pressure in the range of between 0.3 inches $H_2O$ and 1.0 inches $H_2O$.

9. The method of claim 8, further including providing warmed pressurized air to the convective warming device at a flow rate of between 6 cubic feet per minute and 15 cubic feet per minute.

10. A method for warming a person using a forced air warming unit, comprising:
    clothing the person in a clinical garment with a convective warming device mounted therein;
    connecting an air hose between the convective device and the forced air warming unit;
    controlling the temperature of pressurized air produced by the forced air warming unit with a manually-operated remote control unit; and providing warmed pressurized air to the convective warming device at a flow rate of between 6 cubic feet per minute and 15 cubic feet per minute.

11. A comfort warming system, comprising:

a forced air warming unit to provide pressurized air;

a heater in the forced air warming unit;

a control circuit in the forced air warming unit, connected to the heater;

a clinical garment with a convective warming device mounted therein;

an air hose connecting the warming device with the forced air warming unit;

a manually-operated remote control unit external to the forced air warming unit, the remote control unit including a first control for causing the control circuit to control the temperature of the pressurized air emitted in the clinical garment by the convective warming device within a thermal comfort temperature range; and a signal cable mounted to the air hose and connecting the first control to the control circuit.

12. The comfort warming system of claim 11, wherein the remote control unit includes a second control and the signal cable also connects the second control to the control unit for regulating high voltage functions of the forced air warming unit.

13. The comfort warming system of claim 12, wherein the first control includes a hand-operated potentiometer.

14. The comfort warming system of claim 12, wherein the second control includes an on-off switch.

15. The comfort warming system of claim 11, wherein the thermal comfort temperature range is from about 27° C. to about 41° C.

* * * * *

UNITED STATES PATENT AND TRADEMARK OFFICE
CERTIFICATE OF CORRECTION

PATENT NO. : 7,749,261 B2  
APPLICATION NO. : 11/363136  
DATED : July 6, 2010  
INVENTOR(S) : Gary Hansen et al.

Page 1 of 1

It is certified that error appears in the above-identified patent and that said Letters Patent is hereby corrected as shown below:

Column 1
Line 15, delete ""PATENT" and insert -- "PATIENT --, therefor.
Column 2
Line 11 (Approx.), delete "outcomes" and insert -- outcomes. --, therefor.
Column 4
Line 19 (Approx.), delete "unit; details of the forced air warming unit;" and insert -- unit; --, therefor.
Line 62, delete "application" and insert -- applications --, therefor.
Column 5
Line 3-4, delete "his or her microenvironment." And insert -- microenvironment. --, therefor.
Column 9
Line 8, delete "(Stoll A M," and insert -- (Stoll AM, --, therefor.
Line 9, delete "Bewteen" and insert -- Between --, therefor.
Line 16, delete "controlled" and insert -- controlled. --, therefor.
Line 50, delete "H$_2$0" and insert -- H$_2$O --, therefor.
Line 50, delete "H$_2$0." and insert -- H$_2$O. --, therefor.
Column 10
Line 37, in Claim 6, "H$_2$0" and insert -- H$_2$O --, therefor.
Line 38, in Claim 6, "H$_2$0." and insert -- H$_2$O. --, therefor.
Line 54, in Claim 8, "H$_2$0" and insert -- H$_2$O --, therefor.
Line 54, in Claim 8, "H$_2$0." and insert -- H$_2$O. --, therefor.

Signed and Sealed this

Eleventh Day of September, 2012

David J. Kappos
*Director of the United States Patent and Trademark Office*